(12) United States Patent
Christensen, IV et al.

(10) Patent No.: US 7,375,120 B2
(45) Date of Patent: May 20, 2008

(54) PEPTIDE DEFORMYLASE INHIBITORS

(75) Inventors: Siegfried B. Christensen, IV, Collegeville, PA (US); Maxwell D. Cummings, Strafford, PA (US); Jinhwa Lee, Wayne, PA (US); Jia-ning Xiang, Palo Alto, CA (US)

(73) Assignee: Smithkline Beecham Corporation, Philadelphia, PA (US)

( * ) Notice: Subject to any disclaimer, the term of this patent is extended or adjusted under 35 U.S.C. 154(b) by 179 days.

(21) Appl. No.: 10/553,142

(22) PCT Filed: Apr. 16, 2003

(86) PCT No.: PCT/US03/11704

§ 371 (c)(1),
(2), (4) Date: Oct. 14, 2005

(87) PCT Pub. No.: WO2004/098584

PCT Pub. Date: Nov. 18, 2004

(65) Prior Publication Data

US 2006/0229341 A1    Oct. 12, 2006

(51) Int. Cl.
*A61K 31/44*    (2006.01)
*A61K 31/24*    (2006.01)
*A61K 31/235*    (2006.01)
*A61K 31/18*    (2006.01)

(52) U.S. Cl. .................. 514/347; 514/539; 514/542; 514/601; 514/602; 514/603; 514/604; 514/605; 546/293; 560/13; 564/86; 564/95

(58) Field of Classification Search .............. 514/347, 514/539, 542, 601, 602, 603, 604, 605; 546/293; 560/13; 564/86, 95
See application file for complete search history.

(56) References Cited

U.S. PATENT DOCUMENTS 5,985,900 A    11/1999    Bender et al. .............. 514/336
7,022,738 B2*    4/2006    Nakamura et al. .......... 514/604

FOREIGN PATENT DOCUMENTS

JP    2002322197 A    11/2002

OTHER PUBLICATIONS

Database Caplus-Chemical Abstracts Service, Columbus, Ohio. Senju Pharmaceutical: "Peptidylhydroxamic acids and pharmaceuticals containing them". XP002415904. Database Accession No. 2002::847789.

* cited by examiner

*Primary Examiner*—Peter O'Sullivan
(74) *Attorney, Agent, or Firm*—Laura K. Madden; Loretta Sauermelch; Mary McCarthy

(57) ABSTRACT

Novel PDF inhibitors and novel methods for their use are provided.

4 Claims, No Drawings

PEPTIDE DEFORMYLASE INHIBITORS

This application is a 371 of International Application No. PCT/US2003/011704, filed Apr. 16, 2003.

FIELD OF THE INVENTION

The present invention relates to the use of novel antibacterial compounds, and pharmaceutical compositions containing these compounds as peptide deformylase inhibitors.

BACKGROUND OF THE INVENTION

Bacterial initiator methionyl tRNA is modified by methionyl tRNA formyltransferase (FMT) to produce formylmethionyl tRNA. The formyl methionine (f-met) is then incorporated at the N-termini of newly synthesized polypeptides. Polypeptide deformylase (PDF or Def) then deformylates primary translation products to produce N-methionyl polypeptides. Most intracellular proteins are further processed by methionine amino peptidase (MAP) to yield the mature peptide and free methionine, which is recycled. PDF and MAP are both essential for bacterial growth, and PDF is required for MAP activity. This series of reactions is referred to as the methionine cycle (FIG. 1).

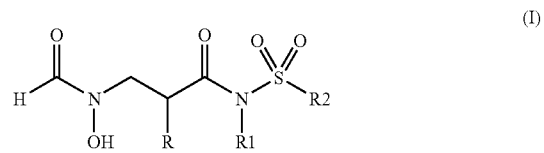

Figure 1. The methionine cycle.

To date, polypeptide deformylase homologous genes have been found in bacteria, in chloroplast-containing plants, in mice and in human. The plant proteins are nuclear encoded but appear to carry a chloroplast localisation signal. This is consistent with the observation that chloroplast RNA and protein synthesis processes are highly similar to those of eubacteria. While there is limited information on protein expression of mammalian PDF gene homologs (Bayer Aktiengesellschaft, Pat. WO2001/42431), no functional role for such proteins has been demonstrated to date (Meinnel, T., Parasitology Today 16(4), 165–168, 2000).

Polypeptide deformylase is found in all eubacteria for which high coverage genomic sequence information is available. Sequence diversity among PDF homologs is high, with as little as 20% identity between distantly related sequences. However, conservation around the active site is very high, with several completely conserved residues, including one cysteine and two histidines which are required to coordinate the active site metal (Meinnel, T. et al., J. Mol. Biol. 267, 749–761, 1997).

PDF is recognized to be an attractive antibacterial target, as this enzyme has been demonstrated to be essential for bacterial growth in vitro (Mazel, D. et al., EMBO J. 13 (4), 914–923, 1994), is not believed to be involved in eukaryotic protein synthesis (Rajagopalan et al., J. Am. Chem. Soc. 119, 12418–12419, 1997), and is universally conserved in prokaryotes (Kozak, M., Microbiol. Rev. 47, 1–45, 1983). Therefore PDF inhibitors can potentially serve as broad spectrum antibacterial agents.

SUMMARY OF THE INVENTION

The present invention involves novel antibacterial compounds represented by Formula (1) hereinbelow and their use as PDF inhibitors.

DETAILED DESCRIPTION OF THE INVENTION

The compounds useful in the present methods are selected from Formula (I) hereinbelow:

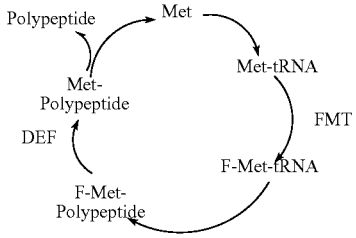

(I)

wherein:
R is selected from the group consisting of:
  $C_{2-6}$ alkyl (optionally substituted by alkoxy, halogen, or $C_{1-3}$ alkylsulfanyl);
  $C_{2-6}$ alkenyl (optionally substituted by alkoxy, halogen, or $C_{1-3}$ alkylsulfanyl);
  $C_{2-6}$ alkynyl (optionally substituted by alkoxy, halogen, or $C_{1-3}$ alkylsulfanyl);
  $(CH_2)_n$—$C_{3-6}$ carbocycle (optionally substituted by alkoxy, halogen, or $C_{1-3}$ alkylsulfanyl); and $(CH_2)_n$—R4, wherein R4 is selected from the group consisting of phenyl, furan, benzofuran, thiophene, benzothiophene, tetrahydrofuran, tetrahydropyran, dioxane, 1,4-benzodioxane or benzo[1,3]dioxole; R4 is optionally substituted by one or more substituent selected from Cl, Br, I, $C_{1-3}$ alkyl (optionally substituted by one to three F) and $C_{1-2}$ alkoxy (optionally substituted by one to three F);
R1 represents hydrogen or $C_{1-4}$ alkyl;
R2 represents $C_{1-6}$ alkyl, Ar$C_{1-4}$ alkyl, wherein substitution is through the alkyl carbon, or Ar;
Ar is selected from the group consisting of phenyl, naphthyl, furyl, pyridyl, thienyl, thiazolyl, isothiazolyl, pyrazolyl, triazolyl, tetrazolyl, imidazolyl, imidazolidinyl, benzofuranyl, indolyl, thiazolidinyl, isoxazolyl, oxadiazolyl, thiadiazolyl, morpholinyl, piperidinyl, piperazinyl, pyrrolyl, and pyrimidyl; all of which may be unsubstituted or substituted by one or more $Z_1$ or $Z_2$ groups;
$Z_1$ and $Z_2$ are, independently, selected from the group consisting of hydrogen, $C_{1-4}$ alkyl, $C_{1-4}$ alkoxy, $(CH_2)_n CO_2R1$, $C(O)NRR1$, $CN$, $(CH_2)_n OH$, $NO_2$, halogen, $NR_2$, and $NHC(O)R2$; and
n is an integer from 0 to 4.

As used herein, the term "alkyl" refers to a straight or branched chain saturated hydrocarbon radical. Examples of "alkyl" as used herein include, but are not limited to, methyl, ethyl, n-propyl, isopropyl, n-butyl, isobutyl, t-butyl, n-pentyl, isopentyl, hexyl and the like.

As used herein, the term "alkenyl" refers to a straight or branched chain hydrocarbon radical having at least one carbon-carbon double bond. Examples of "alkenyl" as used herein include, but are not limited to, ethenyl and propenyl.

As used herein, the term "alkynyl" refers to a straight or branched chain hydrocarbon radical having at least one carbon-carbon triple bond. Examples of "alkynyl" as used herein include, but are not limited to, acetylenyl and 1-propynyl.

As used herein, the term "halogen" refers to fluorine (F), chlorine (Cl), bromine (Br), or iodine (I), and "halo" refers to the halogen radicals fluoro, chloro, bromo and iodo.

As used herein, the term "carbocycle" refers to a non-aromatic cyclic hydrocarbon radical having from three to seven carbon atoms. For carbocycles with five- to seven-membered rings, a ring double bond is allowed. Exemplary "carbocycle" groups include, but are not limited to, cyclopropyl, cyclobutyl, cyclopentyl, cyclopentenyl, cyclohexyl, and cycloheptyl.

As used herein, the term "alkoxy" refers to the group —OR$_a$, where R$_a$ is alkyl as defined above. Exemplary alkoxy groups useful in the present invention include, but are not limited to, methoxy, difluoromethoxy, trifluoromethoxy, ethoxy, n-propoxy, isopropoxy, n-butoxy, and t-butoxy.

As used herein, the term "alkylsulfanyl" refers to the group —SR$_a$, where R$_a$ is alkyl.

Preferred compounds useful in the present invention are selected from the group consisting of:
N-{2-[(Formylhydroxyamino)methyl]heptanoyl}benzenesulfonamide.
4-Chloro-N-{2-[(formylhydroxyamino)methyl]heptanoyl}benzenesulfonamide.
4-tert-Butyl-N-{2-[(formylhydroxyamino)methyl]heptanoyl}benzenesulfonamide.
N-{2-[(Formylhydroxyamino)methyl]heptanoyl}methanesulfonamide.
Butane-1-sulfonic acid {2-[(formylhydroxyamino)methyl]heptanoyl}amide.
Propane-2-sulfonic acid {2-[(formylhydroxyamino)methyl]-heptanoyl}amide.
4-{2-[(Formylhydroxyamino)methyl]heptanoylsulfamoyl}benzoic acid methyl ester.
4-Chloro-N-{2-[(formylhydroxyamino)methyl]-3-phenyl-propanoyl}benzenesulfonamide.
N-{2-[(Formylhydroxyamino)methyl]-3-phenyl-propanoyl}benzenesulfonamide.
5-Methyl-pyridine-2-sulfonic acid {2-[(formylhydroxyamino)methyl]heptanoyl}amide.
N-{2-[(Formylhydroxyamino)methyl]4-phenyl-butanoyl}benzenesulfonamide.
Butane-1-sulfonic acid {2-[(formylhydroxyamino)methyl]-4-phenyl-butanoyl}amide.
Propane-2-sulfonic acid {2-[(formylhydroxyamino)methyl]-3-phenyl-propanoyl}amide.
Biphenyl-4-sulfonic acid {2-[(formylhydroxyamino)methyl]heptanoyl}amide.
5-Dimethylamino-naphthalene-1-sulfonic acid {2-[(formylhydroxyamino)methyl]heptanoyl}amide.
4-{2-[(Formylhydroxyamino)methyl]heptanoylsulfamoyl}benzoic acid propyl ester.
Naphthalene-1-sulfonic acid {2-[(formylhydroxyamino)methyl]heptanoyl}amide.
N-{2-[(Formylhydroxyamino)methyl]-5-methyl-hexanoyl}benzenesulfonamide.
5-Methyl-pyridine-2-sulfonic acid {2-[(formylhydroxyamino)methyl]-5-methyl-hexanoyl}amide.
4-Dimethylamino-N-{2-[(formylhydroxyamino)methyl]-5-methyl-hexanoyl}benzenesulfonamide.
N-[2-(2,6-Dichloro-benzyl)-3-(formylhydroxyamino)propanoyl]benzenesulfonamide.
Dimethylamino-N-{2-[(formylhydroxyamino)methyl]heptanoyl}benzenesulfonamide.
5-Methyl-pyridine-2-sulfonic acid [2-(2,6-dichlorobenzyl)-3-(formylhydroxyamino)propanoyl]amide.
5-Dimethylamino-naphthalene-1-sulfonic acid [2-(2,6-dichlorobenzyl)-3-(formylhydroxyamino)propanoyl]amide.
N-{2-[(Formylhydroxyamino)methyl]heptanoyl}-4-methyl-benzenesulfonamide.
N-{2-[(Formylhydroxyamino)methyl]heptanoyl}-4-phenoxy-benzenesulfonamide.
N-{2-[(Formylhydroxyamino)methyl]heptanoyl}-4-methoxy-benzenesulfonamide.
5-Methyl-pyridine-2-sulfonic acid {3-(3,4-dichlorophenyl)-2-[(formylhydroxyamino)methyl]propanoyl}amide.
N-{2-[(Formylhydroxyamino)methyl]hexanoyl}benzenesulfonamide.
5-Dimethylamino-naphthalene-1-sulfonic acid {2-[(formylhydroxyamino)methyl]hexanoyl}amide.
N-{2-[(Formylhydroxyamino)methyl]hexanoyl}-4-phenoxy-benzenesulfonamide.
5-Dimethylamino-naphthalene-1-sulfonic acid {2-[(formylhydroxyamino)methyl]-3-methyl-butanoyl}amide.
5-Dimethylamino-naphthalene-1-sulfonic acid {(R)-2-[(formylhydroxyamino)methyl]heptanoyl}amide.
5-Dimethylamino-naphthalene-1-sulfonic acid {2-[(formylhydroxyamino)methyl]pentanoyl}amide.
Biphenyl-4-sulfonic acid {2-[(formylhydroxyamino)methyl]pentanoyl}amide.
Biphenyl-4-sulfonic acid {2-[(formylhydroxyamino)methyl]-4-methyl-pentanoyl}amide.
5-Dimethylamino-naphthalene-1-sulfonic acid {2-[(formylhydroxyamino)methyl]-4-methyl-pentanoyl}amide.

Also included in the present invention are pharmaceutically acceptable salts and complexes. Preferred are the hydrochloride, hydrobromide and trifluoroacetate salts. The compounds of the present invention may contain one or more asymmetric carbon atoms and may exist in racemic and optically active forms. All of these compounds and diastereomers are contemplated to be within the scope of the present invention.

The compounds and processes of the present invention will be better understood in connection with the following synthetic schemes, which are merely illustrative of the methods by which the compounds of the invention may be prepared and are not intended to limit the scope of the invention as defined in the appended claims.

The present invention provides compounds of formula (I),

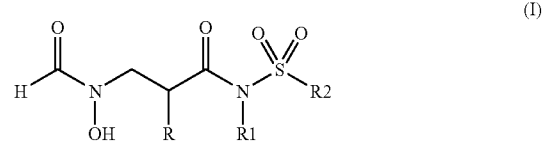

(I)

that can be prepared by reacting a mono-substituted dialkyl malonate of Formula (2)

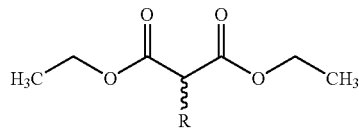
(2)

with a base, such as potassium hydroxide, in an appropriate solvent, such as ethanol/water, to afford a mono-acid of Formula (3).

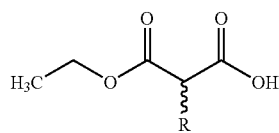
(3)

Coupling of a mono-acid of Formula (3) with benzylhydroxyamine in the presence of a coupling reagent, such as 1-[3-(dimethylamino)propyl]-3-ethylcarbodiimide hydrochloride, and a base, such as 4-(dimethylamino)pyridine, in an appropriate solvent, such as dichloromethane, gives an amide of Formula (4).

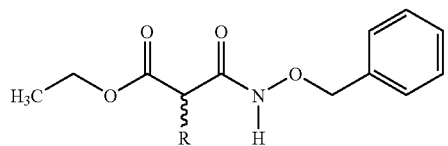
(4)

Reduction of the ester of a compound of the Formula (4) with a reducing agent, such as lithium borohydride, in an appropriate solvent, such as tetrahydrofuran, at room temperature provides an alcohol of Formula (5).

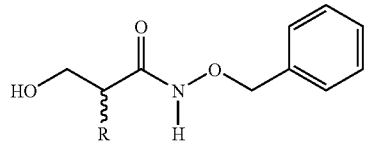
(5)

Treatment of an alcohol of Formula (5) under Mitsunobu conditions affords a lactam of Formula (6).

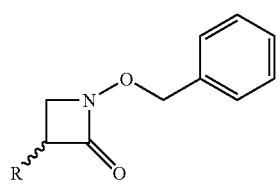
(6)

Hydrolysis of a lactam of Formula (6) using, e.g., lithium hydroxide in an appropriate solvent mixture, such as THF—H$_2$O-MeOH, gives an acid of Formula (7).

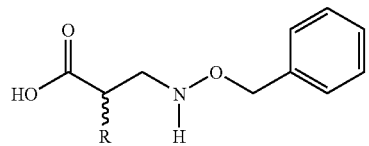
(7)

Formylation of the amine of a compound of the Formula (7) is achieved using formic acid and acetic anhydride in a solvent, such as dichloromethane, to provide a formylated compound of Formula (8).

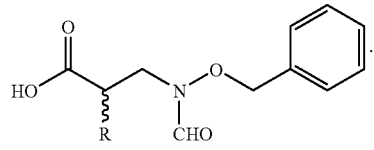
(8)

Coupling of the acid of a compound of the Formula (8) with a sulfonamide of Formula (9)

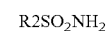
R2SO$_2$NH$_2$ (9)

in the presence of appropriate coupling reagents, as mentioned above, affords an acyl sulfonamide of Formula (10).

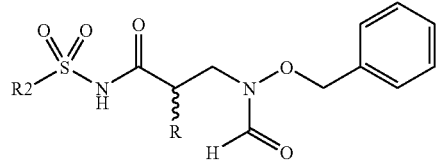
(10)

Hydrogenolysis to remove the benzyl group using a catalyst, such as 10% Pd/C, in an appropriate solvent, such as ethanol, gives a compound of Formula (I) wherein R1=H.

Any racemates can be resolved at the level of any intermediate during the synthesis or at the level of the final product using, e.g., a chiral chromatography method, to provide a compound of Formula (I) in each of two enantiomeric forms.

Alternatively, an enantiomerically pure compound of Formula (I) can be prepared by reacting an appropriately protected hydroxy acid chloride of Formula (11) wherein P is a protecting group,

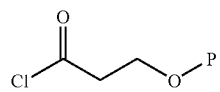
(11)

with a chiral agent, such as Evan's chiral oxazolidinone, in the presence of a base to afford a chiral ester of Formula (12).

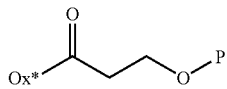

Treatment of an ester of Formula (12) with a base, such as lithium diisopropylamide, in a sovent, such as tetrahydrofuran, followed by addition of an electrophile, such as RX, to provide either of two chiral compounds (13) and (14) depending on the selection of chiral oxazolidinone.

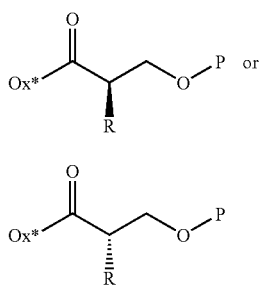

Conversion of a compound of Formula (13) or (14) to benzyloxyamine (15) or (16), respectively can be achieved by a sequence comprising: i) deprotection; ii) mesylation or triflation; and iii) displacement by benzylhydroxylamine.

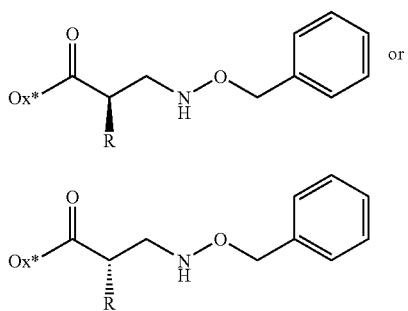

Hydrolysis of an ester of Formula (15) or (16) using, e.g., lithium hydroxide and hydrogen peroxide, in an appropriate solvent gives the corresponding acid of Formula (17) or (18), respectively.

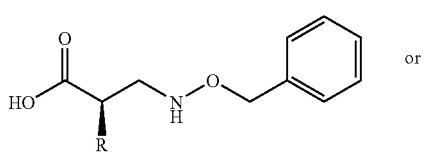

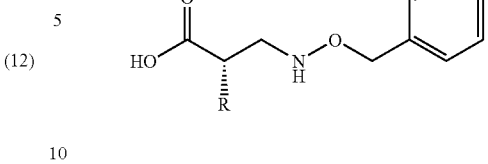

An acid of Formula (17) or (18) is converted to an enantiomerically pure compound of Formula (I) using the same reaction methods described above.

SYNTHETIC EXAMPLES

The invention will now be described by reference to the following examples which are merely illustrative and are not to be construed as a limitation of the scope of the present invention.

As used herein the symbols and conventions used in these processes, schemes and examples are consistent with those used in the contemporary scientific literature, for example, the *Journal of the American Chemical Society* or the *Journal of Biological Chemistry*. Unless otherwise noted, all starting materials were obtained from commercial suppliers and used without further purification.

All references to ether are to diethyl ether; brine refers to a saturated aqueous solution of NaCl. Unless otherwise indicated, all temperatures are expressed in ° C. (degrees Centigrade). All reactions are conducted under an inert atmosphere at room temperature unless otherwise noted, and all solvents are highest available purity unless otherwise indicated.

$^1$H NMR (hereinafter also "NMR") spectra were recorded on a Varian VXR-300, a Varian Unity-300, a Varian Unity-400 instrument, a Brucker AVANCE-400, a General Electric QE-300 or a Bruker AM 400 spectrometer. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), quint (quintet), m (multiplet), br (broad).

Mass spectra were run on an open access LC-MS system using electrospray ionization. LC conditions: 4.5% to 90% CH$_3$CN (0.02% TFA) in 3.2 min with a 0.4 min hold and 1.4 min re-equilibration; detection by MS, UV at 214 nm, and a light scattering detector (ELS). Column: 1×40 mm Aquasil (C18).

For preparative (prep) hplc, circa 50 mg of the final products were injected in 500 uL of DMSO onto a 50×20 mm I. D. YMC CombiPrep ODS-A column at 20 mL/min with a 10 min gradient from 10% CH$_3$CN (0.1% TFA) to 90% CH$_3$CN (0.1% TFA) in H$_2$O (0.1% TFA) and a 2 min hold. Flash chromatography was run over Merck Silica gel 60 (230–400 mesh).

Infrared (IR) spectra were obtained on a Nicolet 510 FT-IR spectrometer using a 1-mm NaCl cell. Most of the reactions were monitored by thin-layer chromatography on 0.25 mm E. Merck silica gel plates (60F-254), visualized with UV light, 5% ethanolic phosphomolybdic acid or p-anisaldehyde solution.

Example 1

N-{2-[(Formylhydroxyamino)methyl]heptanoyl}benzenesulfonamide

Preparation 1. 2-Pentylmalonic acid, monoethyl ester

To diethyl pentylmalonate (15.0 g, 65.1 mmol) in THF (150 mL) was added dropwise at 0° C. KOH (3.65 g, 65.1 mmol) in H$_2$O (50 mL). After stirring at room temperature overnight, the reaction was quenched with water (150 mL) and extracted using ether (200 mL×2). The aqueous layer was acidified with 3 N HCl, and extracted with ether (200 mL×2). The combined organic layers were washed with brine, and dried over MgSO$_4$. Removal of the solvent under reduced pressure yielded 9.40 g (71%) of the title compound. $^1$H NMR (400 MHz, CDCl$_3$) δ 10.0 (br s, 1H), 4.21 (q, J=7.2 Hz, 2H), 3.39 (t, J=7.5 Hz, 1H), 1.93 (m, 2H), 1.39–1.28 (m, 9H), 0.90 (t, J=6.8 Hz, 3H). MH+ 203.

Preparation 2. 2-Benzyloxycarbamoylheptanoic acid, ethyl ester

To a mixture of 2-pentyl-malonic acid, monoethyl ester (9.4 g, 46.53 mmol), benzylhydroxyamine hydrochloride (7.4 g, 46.53 mmol) and 4-(dimethylamino)pyridine (11.9 g, 97.71 mmol) in dichloromethane (150 mL) was added at 0° C. 1-[3-(dimethylamino)propyl]-3-ethylcarbodiimide hydrochloride (8.9 g, 46.53 mmol). After stirring at room temperature overnight, the reaction was quenched with 1N HCl and extracted using dichloromethane (150 mL×2). The organic extracts were washed with water, brine, and dried over MgSO$_4$. After removing the solvent under reduced pressure, purification by flash column chromatography using an eluting system of hexane/EtOAc (2:1) yielded 12.9 g (90%) of the title compound. $^1$H NMR (400 MHz, CDCl$_3$) δ 8.86 (br s, 1H), 7.20 (s, 5H), 4.85 (s, 2H), 4.08 (q, J=6.9 Hz, 2H), 3.06 (t, J=7.2 Hz, 1H), 1.78 (m, 2H), 1.22–1.66 (m, 9H), 0.80 (t, J=6.7 Hz, 3H). MH+ 308.

Preparation 3. 2-Hydroxymethylheptanoic acid, benzyloxyamide

To a solution of 2-benzyloxycarbamoylheptanoic acid, ethyl ester (12.29 g, 39.98 mmol) in THF (400 mL)) was added LiBH$_4$ (8.70 g, 399.8 mmol) at room temperature. The resulting mixture was stirred at room temperature overnight. Ice-water (500 mL) was then added to the reaction mixture (warning: vigorous evolution of gas). The aqueous layer was extracted with EtOAc (400 mL×2). The organic extracts were washed with water, brine, and dried over MgSO$_4$. After removing the solvent under reduced pressure, flash column chromatography (hexane:EtOAc 1/2) yielded 5.36 g (51%) of the title compound. $^1$H NMR (400 MHz, CHCl) δ 9.22 (br s, 1H), 7.41–7.28 (m, 5H), 4.89 (q, J=10.6 Hz, 2H), 3.70–3.37 (m, 3H), 2.17 (m, 1H). 1.54 (br s, 1H), 1.27 (m, 6H), 0.88 (t, J=6.9 Hz). MH+ 266.

Preparation 4. 1-Benzyloxy-3-pentylazetidin-2-one

To a mixture of 2-hydroxymethyl-heptanoic acid benzyloxyamide (5.36 g, 20.23 mmol) and triphenylphosphine (5.31 g, 20.23 mmol) in THF (200 mL) at 0° C. was added dropwise diethyl azodicarboxylate (3.3 mL, 20.23 mmol). The reaction stirred at room temperature overnight. The reaction was then quenched by adding water (200 mL). The aqueous layer was extracted with EtOAc (200 mL×2). The combined organic layer was washed with brine, and dried over MgSO$_4$. After removing the solvent under vacuum, the residue was purified by flash column chromatography (hexane:EtOAc 5/1) to provide the title compound (4.68 g, 94%). $^1$H NMR (400 MHz, CHCl$_3$) δ 7.35–7.25 (m, 5H), 4.87 (s, 2H), 3.28 (t, J=4.85 Hz, 1H), 2.84 (q, J=2.35 Hz, 1H), 2.77 (m, 1H), 1.62 (m, 1H), 1.36 (m, 1H), 1.25 –1.16 (m, 6H), 0.88 (t, J=6.9 Hz, 3H). MH+ 248.

Preparation 5. 2-(Benzyloxyamino-methyl)heptanoic acid

To 1-benzyloxy-3-pentylazetin-2-one (1.82 g, 7.37 mmol) in a mixture of THF—H$_2$O-MeOH (100 mL, 3:1:1 v/v) was added LiOH monohydrate (3.60 g, 73.68 mmol). After stirring at room temperature overnight, water (50 mL) was added to the mixture. The solution was acidified to pH 6 with 3N HCl and extracted with EtOAc (100 mL×2). The combined organic layers were dried over MgSO$_4$, and evaporated under vacuum to yield the title compound (1.60 g, 82%). $^1$H NMR (400 MHz, CHCl$_3$) δ 9.80 (br s, 1H), 7.37 (m, 5H), 4.75 (m, 2H), 3.14 (m, 2H), 2.74 (m, 1H), 170 (m, 1H), 1.53 (m, 1H), 1.38–1.25 (m, 6H), 0.91 (t, J=6.8 Hz, 3H). MH+ 266.

Preparation 6. 2-[(Benzyloxyformylamino)methyl]heptanoic acid

To a cold solution of 2-(benzyloxyaminomethyl)heptanoic acid (1.57 g, 5.92 mmol) in HCO$_2$H (29 mL) and dichloromethane (29 mL) was added acetic anhydride (5.9 mL, 62.75 mmol) at 0° C. The mixture was stirred at 0° C. for 3 hours. The volatiles were removed by evaporation under vacuum. Dichloromethane (50 mL) was added to the residue, and the solution was washed with brine, and dried over MgSO$_4$. Filtration and evaporation under vacuum provided the title compound (1.73 g, 100%). $^1$H NMR (400 MHz, CHCl$_3$) δ 8.07 (br s, 1H), 7.29 (m, 5H), 4.91–4.71 (m, 2H), 3.76 (m, 2H), 2.67 (m, 1H), 1.54 (m, 1H), 1.41(m, 1H), 1.20 (m, 6H), 0.80 (t, J=7.0 Hz, 3H). MH+ 294.

Preparation 7. N-{2-[Benzyloxyformylamino)methyl]heptanoyl}benzenesulfonamide To 2-[(benzyloxyformylamino)methyl]heptanoic acid (94 mg, 0.320 mmol), benzenesulfonamide (51 mg, 0.320 mmol) and 4-(dimethylamino)pyridine (40 mg, 0.320 mmol) in dichloromethane (4 mL) was added at 0° C. 1-[3-(dimethylamino)-propyl]-3-ethylcarbodiimide hydrochloride (62 mg, 0.320 mmol). After stirring at room temperature overnight, the reaction was quenched with 1N HCl and extracted using dichloromethane (15 mL×2). The organic extracts were washed with water, brine, and dried over MgSO$_4$. After removing the solvent under reduced pressure, purification by flash column chromatography using EtOAc yielded 130 mg (94%) of the title compound. $^1$H NMR (400 MHz, CHCl) δ 9.80 (br s, 1H), 8.10–7.10 (m, 12H), 4.60–4.30 (m, 2H), 3.70–3.30 (m, 2H), 2.54 (m, 1H), 1.44 (m, 1H), 1.33(m, 1H), 1.08 (m, 6H), 0.73 (t, J=6.8 Hz, 3H). MH+ 433.

N-{2-[(Formylhydroxyamino)methyl]heptanoyl}benzenesulfonamide

To N-{2-[benzyloxyformylamino)methyl]heptanoyl}benzenesulfonamide (130 mg, 0.301 mmol) in EtOH (5 mL) was added 10% Pd/C (25 mg). The reaction mixture was subjected to hydrogenation overnight at room temperature. After the reaction was completed, the reaction mixture was filtered through a pad of Celite, and washed with EtOH (5 mL×3). Removal of the solvent provided the crude product, which was further purified by HPLC to yield the title compound (38 mg, 37%). $^1$H NMR (400 MHz, CHCl$_3$) δ 9.80 (br s, 1H), 7.98–7.46 (m, 6H), 4.06 (m, 1H), 3.62 (m, 1H), 2.75 (m, 1H), 1.51 (m, 1H), 1.30 (m, 1H), 1.19–1.12 (m, 6H), 0.75 (t, J=6.7 Hz, 3H). MH+ 343.

Example 2

4-Chloro-N-{2-[(formylhydroxyamino)methyl]heptanoyl}benzenesulfonamide

The title compound was prepared following the procedures of Example 1 except that 4-chlorobenzenesulfonamide was used in place of benzenesulfonamide. After the final debenzylation, purification by preparative HPLC yielded 40 mg (43%) of the title compound. $^1$H NMR (400 MHz, CHCl$_3$) δ 8.00 (d, J=8.4 Hz, 2H), 7.72 (s, 1H), 7.52 (d, J=8.4 Hz, 2H), 3.72 (m, 1H), 3.48 (m, 1H), 2.89 (br s, 1H), 1.59 (m, 1H), 1.38 (m, 1H), 1.30–1.19 (m, 6H), 0.83 (t, J=6.6 Hz, 3H). MH+ 377.

Example 3

4-tert-Butyl-N-{2-[(formylhydroxyamino)methyl]heptanoyl}benzenesulfonamide

The title compound was prepared following the procedures of Example 1 except that 4-tert-butylbenzenesulfonamide was used in place of benzenesulfonamide. After the final debenzylation, purification by preparative HPLC yielded 70 mg (66%) of the title compound. $^1$H NMR (400 MHz, CDCl$_3$) δ 9.70 (br s, 1H), 7.97 (d, J=8.6 Hz, 2H), 7.71 (s, 1H), 3.72 (m, 1H), 3.47 (m, 1H), 2.91 (br s, 1H), 1.56 (m, 1H), 1.36 (m, 1H), 1.35 (s, 9H), 1.17 (m, 6H), 0.80 (t, J=6.7 Hz, 3H). MH+ 399.

Example 4

N-{2-[(Formylhydroxyamino)methyl]heptanoyl}methanesulfonamide

The title compound was prepared following the procedures of Example 1, except that methanesulfonamide was used in place of benzenesulfonamide. After the final debenzylation, purification by preparative HPLC yielded 47 mg (24%) of the title compound. $^1$H NMR (400 MHz, CDCl$_3$) δ •9.70 (br s, 1H), 7.88 (s, 1H), 3.87 (dd, J=15.2, 11.6 Hz, 1H), 3.53 (d, J=11.6 Hz, 1H), 2.91 (br s, 1H), 1.70 (m, 1H), 1.47 (m, 1H), 1.30 (m, 6H), 0.90 (t, J=6.8 Hz, 3H). MH+ 281.

Example 5

Butane-1-sulfonic acid {2-[(formylhydroxyamino)methyl]heptanoyl}amide

The title compound was prepared following the procedures of Example 1, except that butane-1-sulfonic acid amide was used in place of benzenesulfonamide. After the final debenzylation, purification by preparative HPLC yielded 94 mg (50%) of the title compound. $^1$H NMR (400 MHz, CDCl$_3$) δ δ 9.70 (br s, 1H), 7.86 (s, 1H), 3.84 (m, 1H), 3.54–3.38 (m, 3H), 2.91 (br s, 1H), 1.81–1.32 (m, 12H), 0.96 (t, J=7.3 Hz, 3H), 0.90 (t, J=6.9 Hz, 3H). MH+ 545.

Example 6

Propane-2-sulfonic acid {2-[(formylhydroxyamino)methyl]heptanoyl}amide MH+ 309

Example 7

4-{2-[(Formylhydroxyamino)methyl]heptanoylsulfamoyl}benzoic acid methyl ester. MH+ 401

Example 8

4-Chloro-N-{2-[(formylhydroxyamino)methyl]-3-phenyl-propanoyl}benzenesulfonamide. MH+ 398

Example 9

N-{2-[(Formylhydroxyamino)methyl]-3-phenyl-propanoyl}benzenesulfonamide. MH+ 363

Example 10

5-Methyl-pyridine-2-sulfonic acid {2-[(formylhydroxyamino)methyl]heptanoyl}amide. MH+ 358

Example 11

N-{2-[(Formylhydroxyamino)methyl]-4-phenylbutanoyl}benzenesulfonamide. MH+ 377

Example 12

Butane-1-sulfonic acid {2-[(formylhydroxyamino)methyl]-4-phenylbutanoyl}amide. MH+ 357

Example 13

Propane-2-sulfonic acid {2-[(formylhydroxyamino)methyl]-3-phenylpropanoyl}amide. MH+ 329

Example 14

Biphenyl-4-sulfonic acid {2-[(formylhydroxyamino)methyl]heptanoyl}amide. MH+ 419

Example 15

5-Dimethylamino-naphthalene-1-sulfonic acid {2-[(formylhydroxyamino)methyl]heptanoyl}amide. MH+ 436

Example 16

4-{2-[(Formylhydroxyamino)methyl]heptanoylsulfamoyl}benzoic acid propyl ester. MH+ 429

Example 17

Naphthalene-1-sulfonic acid {2-[(formylhydroxyamino)methyl]heptanoyl}amide. MH+ 393

Example 18

N-{2-[(Formylhydroxyamino)methyl]-5-methylhexanoyl}benzenesulfonamide. MH+ 343

Example 19

5-Methyl-pyridine-2-sulfonic acid {2-[(formylhydroxyamino)methyl]-5-methylhexanoyl}amide. MH+ 358

Example 20

4-Dimethylamino-N-{2-[(formylhydroxyamino)methyl]-5-methylhexanoyl}benzenesulfonamide. MH+ 386

Example 21

N-[2-(2,6-Dichlorobenzyl)-3-(formylhydroxyamino)propanoyl]benzenesulfonamide. MH+ 432

Example 22

Dimethylamino-N-{2-[(formylhydroxyamino)methyl]heptanoyl}benzenesulfonamide. MH+ 386

Example 23

5-Methyl-pyridine-2-sulfonic acid [2-(2,6-dichlorobenzyl)-3-(formylhydroxyamino)propanoyl]amide. MH+ 447

Example 24

5-Dimethylamino-naphthalene-1-sulfonic acid [2-(2,6-dichlorobenzyl)-3-(formylhydroxyamino)propanoyl]amide. MH+ 524

Example 25

N-{2-[(Formylhydroxyamino)methyl]heptanoyl}-4-methyl benzenesulfonamide. MH+ 357

Example 26

N-{2-[(Formylhydroxyamino)methyl]heptanoyl}-4-phenoxy benzenesulfonamide. MH+ 435

Example 27

N-{2-[(Formylhydroxyamino)methyl]heptanoyl}-4-methoxy benzenesulfonamide. MH+ 373

Example 28

5-Methyl-pyridine-2-sulfonic acid {3-(3,4-dichlorophenyl)-2-[(formylhydroxyamino)methyl]propanoyl}amide. MH+ 447

Example 29

N-{2-[(Formylhydroxyamino)methyl]hexanoyl}benzenesulfonamide. MH+ 329

Example 30

5-Dimethylamino-naphthalene-1-sulfonic acid {2-[(formylhydroxyamino)methyl]hexanoyl}amide. MH+ 422

Example 31

N-{2-[(Formylhydroxyamino)methyl-hexanoyl}4-phenoxybenzenesulfonamide. MH+ 421

Example 32

5-Dimethylamino-naphthalene-1-sulfonic acid {2-[(formylhydroxyamino)methyl]-3-methylbutanoyl}amide. MH+ 408

Example 33

5-Dimethylamino-naphthalene-1-sulfonic acid {(R)-2-[(formylhydroxyamino)methyl]heptanoyl}amide. MH+ 436

Example 34

5-Dimethylamino-naphthalene-1-sulfonic acid {2-[(formylhydroxyamino)methyl]pentanoyl}amide. MH+ 408

Example 35

Biphenyl-4-sulfonic acid {2-[(formylhydroxyamino)methyl]pentanoyl}amide. MH+ 391

Example 36

Biphenyl-4-sulfonic acid {2-[(formylhydroxyamino)methyl]-4-methylpentanoyl}amide. MH+ 405

Example 37

5-Dimethylamino-naphthalene-1-sulfonic acid {2-[(formylhydroxyamino)methyl]-4-methylpentanoyl}amide. MH+ 422

With appropriate manipulation and protection of any chemical functionality, synthesis of the remaining compounds of Formula (I) is accomplished by methods analogous to those above and to those described in the Experimental section.

Compositions, Administration and Biological Assays

Compounds of Formula (1) and their pharmaceutically acceptable salts may be administered in a standard manner for antibiotics, for example orally, parenterally, sub-lingually, dermally, transdermally, rectally, via inhalation or via buccal administration.

Compositions of Formula (1) and their pharmaceutically acceptable salts which are active when given orally can be formulated as syrups, tablets, capsules, creams and lozenges. A syrup formulation will generally consist of a suspension or solution of the compound or salt in a liquid carrier for example, ethanol, peanut oil, olive oil, glycerine or water with a flavoring or coloring agent. Where the composition is in the form of a tablet, any pharmaceutical carrier routinely used for preparing solid formulations may be used.

Examples of such carriers include magnesium stearate, terra alba, talc, gelatin, acacia, stearic acid, starch, lactose and sucrose. Where the composition is in the form of a capsule, any routine encapsulation is suitable, for example, using the aforementioned carriers in a hard gelatin capsule shell. Where the composition is in the form of a soft gelatin shell capsule, any pharmaceutical carrier routinely used for preparing dispersions or suspensions may be considered, for example, aqueous gums, celluloses, silicates or oils, and incorporated in a soft gelatin capsule shell.

Typical parenteral compositions consist of a solution or suspension of a compound or salt in a sterile aqueous or non-aqueous carrier optionally containing a parenterally acceptable oil, for example, polyethylene glycol, polyvinylpyrrolidone, lecithin, arachis oil or sesame oil.

Typical compositions for inhalation are in the form of a solution, suspension or emulsion that may be administered as a dry powder or in the form of an aerosol using a conventional propellant such as dichlorodifluoromethane or trichlorofluoromethane.

A typical suppository formulation comprises a compound of Formula (1) or a pharmaceutically acceptable salt thereof which is active when administered in this way, with a binding and/or lubricating agent, for example, polymeric glycols, gelatins, cocoa-butter or other low melting vegetable waxes or fats or their synthetic analogs.

Typical dermal and transdermal formulations comprise a conventional aqueous or non-aqueous vehicle, for example, a cream, ointment, lotion or paste or are in the form of a medicated plaster, patch or membrane.

Preferably the composition is in unit dosage form, for example a tablet, capsule or metered aerosol dose, so that the patient may administer a single dose.

Each dosage unit for oral administration contains suitably from 0.1 mg to 500 mg/Kg, and preferably from 1 mg to 100 mg/Kg, and each dosage unit for parenteral administration contains suitably from 0.1 mg to 100 mg/Kg, of a compound of Formula (1) or a pharmaceutically acceptable salt thereof calculated as the free acid. Each dosage unit for intranasal administration contains suitably 1–400 mg and preferably 10 to 200 mg per person. A topical formulation contains suitably 0.01 to 5.0% of a compound of Formula (1).

The daily dosage regimen for oral administration is suitably about 0.01 mg/Kg to 40 mg/Kg of a compound of Formula (1) or a pharmaceutically acceptable salt thereof calculated as the free acid. The daily dosage regimen for parenteral administration is suitably about 0.001 mg/Kg to 40 mg/Kg of a compound of Formula (1) or a pharmaceutically acceptable salt thereof calculated as the free acid. The daily dosage regimen for intranasal administration and oral inhalation is suitably about 10 to about 500 mg/person. The active ingredient may be administered from 1 to 6 times a day, sufficient to exhibit the desired activity.

No unacceptable toxicological effects are expected when compounds of the present invention are administered in accordance with the present invention.

The biological activity of the compounds of Formula (1) are demonstrated by the following test:

Biological Assay

S. aureus or E. coli PDF activity is measured at 25° C., using a continuous enzyme-linked assay developed by Lazennec & Meinnel ("Formate dehydrogenase-coupled spectrophotometric assay of peptide deformylase", Anal. Biochem. 1997, 244, pp. 180–182), with minor modifications. The reaction mixture is contained in 50 uL with 50 mM potassium phosphate buffer (pH 7.6), 15 mM NAD, 0.25 U formate dehydrogenase. The substrate peptide, f-Met-Ala-Ser, is included at the $K_M$ concentration. The reaction is triggered with the addition of 10 nM Def1 enzyme, and absorbance is monitored for 20 min at 340 nm.

Antimicrobial Activity Assay

Whole-cell antimicrobial activity was determined by broth microdilution using the National Committee for Clinical Laboratory Standards (NCCLS) recommended procedure, Document M7-A4, "Methods for Dilution Susceptibility Tests for Bacteria that Grow Aerobically" (incorporated by reference herein). The compound was tested in serial two-fold dilutions ranging from 0.06 to 64 mcg/ml. A panel of 12 strains were evaluated in the assay. This panel consisted of the following laboratory strains: *Staphylococcus aureus* Oxford, *Staphylococcus aureus* WCUH29, *Enterococcus faecalis* I, *Enterococcus faecalis* 7, *Haemophilus influenzae* Q1, *Haemophilus influenzae* NEMC1, *Moraxella catarrhalis* 1502, *Streptococcus pneumoniae* 1629, *Streptococcus pneumoniae* N1387, *Streptococcus pneumoniae* N1387, *E. coli* 7623 (AcrABEFD+) and *E. coli* 120 (AcrAB–). The minimum inhibitory concentration (MIC) was determined as the lowest concentration of compound that inhibited visible growth. A mirror reader was used to assist in determining the MIC endpoint.

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A compound according to formula (I):

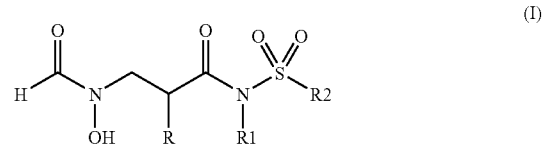

wherein:
R is selected from the group consisting of:
C$_{2-6}$ alkyl (optionally substituted by alkoxy, halogen, or C$_{1-3}$ alkylsulfanyl);
C$_{2-6}$ alkenyl (optionally substituted by alkoxy, halogen, or C$_{1-3}$ alkylsulfanyl);
C$_{2-6}$ alkynyl (optionally substituted by alkoxy, halogen, or C$_{1-3}$ alkylsulfanyl);
(CH$_2$)$_n$—C$_{3-6}$ carbocycle (optionally substituted by alkoxy, halogen, or C$_{1-3}$ alkylsulfanyl); and (CH$_2$)$_n$—R4, wherein R4 is selected from the group consisting of phenyl, furan, benzofuran, thiophene, benzothiophene, tetrahydrofuran, tetrahydropyran, dioxane, 1,4-benzodioxane and benzo[1,3]dioxole; R4 is optionally substituted by one or more substituents selected from Cl, Br, I, $C_{1-3}$ alkyl (optionally substituted by one to three F) and $C_{1-2}$ alkoxy (optionally substituted by one to three F);

R1 represents hydrogen or $C_{1-4}$ alkyl;

R2 represents $C_{1-6}$ alkyl, $ArC_{1-4}$ alkyl, wherein substitution is through the alkyl carbon, or Ar;

Ar is selected from the group consisting of phenyl, naphthyl, furyl, pyridyl, thienyl, thiazolyl, isothiazolyl, pyrazolyl, triazolyl, tetrazolyl, imidazolyl, imidazolidinyl, benzofuranyl, indolyl, thiazolidinyl, isoxazolyl, oxadiazolyl, thiadiazolyl, morpholinyl, piperidinyl, piperazinyl, pyrrolyl, and pyrimidyl; all of which may be unsubstituted or substituted by one or more $Z_1$ or $Z_2$ groups;

$Z_1$ and $Z_2$ are, independently, selected from the group consisting of hydrogen, $C_{1-4}$ alkyl, $C_{1-4}$ alkoxy, $(CH_2)_n CO_2R1$, $C(O)NRR1$, $CN$, $(CH_2)_nOH$, $NO_2$, halogen, $NHR_2$, and $NHC(O)R2$; and n is an integer from 0 to 4; or a pharmaceutically acceptable salt thereof.

2. A compound according to claim 1 selected from the group consisting of:

N-{2-[(Formylhydroxyamino)methyl]heptanoyl}benzenesulfonamide;

4-Chloro-N-{2-[(formylhydroxyamino)methyl]heptanoyl}benzenesulfonamide;

4-tert-Butyl-N-{2-[(formylhydroxyamino)methyl]heptanoyl}benzenesulfonamide;

N-{2-[(Formylhydroxyamino)methyl]heptanoyl}methanesulfonamide;

Butane-1-sulfonic acid {2[(formylhydroxyamino)methyl]heptanoyl}amide;

Propane-2-sulfonic acid {2-[(formylhydroxyamino)methyl]-heptanoyl}amide;

4-{2-[(Formylhydroxyamino)methyl]heptanoylsulfamoyl}benzoic acid methyl ester;

4-Chloro-N-{2-[(formylhydroxyamino)methyl]-3-phenyl-propanoyl}benzenesulfonamide;

N-{2-[(Formylhydroxyamino)methyl]-3-phenyl-propanoyl}benzenesulfonamide;

5-Methyl-pyridine-2-sulfonic acid {2-[(formylhydroxyamino)methyl]heptanoyl}amide;

N-{2-[(Formylhydroxyamino)methyl]-4-phenyl-butanoyl}benzenesulfonamide;

Butane-1-sulfonic acid {2-[(formylhydroxyamino)methyl]-4-phenyl-butanoyl}amide;

Propane-2-sulfonic acid {2-[(formylhydroxyamino)methyl]-3-phenyl-propanoyl}amide;

Biphenyl-4-sulfonic acid {2-[(formyl-hydroxy-amino)-methyl]-heptanoyl}amide;

5-Dimethylamino-naphthalene-1-sulfonic acid {2-[(formylhydroxyamino) methyl]heptanoyl}amide;

4-{2-[(Formylhydroxyamino)methyl]heptanoylsulfamoyl}benzoic acid propyl ester;

Naphthalene-1-sulfonic acid {2-[(formylhydroxyamino)methyl]heptanoyl}amide;

N-{2-[(Formylhydroxyamino)methyl]-5-methylhexanoyl}benzenesulfonamide;

5-Methyl-pyridine-2-sulfonic acid {2-[(formylhydroxyamino)methyl]-5-methyl-hexanoyl}amide;

4-Dimethylamino-N-{2-[(formylhydroxyamino)methyl]-5-methyl-hexanoyl}benzenesulfonamide;

N-[2-(2,6-Dichloro-benzyl)-3-(formylhydroxyamino)propanoyl]benzenesulfonamide;

Dimethylamino-N-{2-[((formylhydroxyamino)methyl]heptanoyl}benzenesulfonamide;

5-Methyl-pyridine-2-sulfonic acid [2-(2,6-dichlorobenzyl)-3-(formylhydroxyamino)propanoyl]amide;

5-Dimethylamino-naphthalene-1-sulfonic acid [2-(2,6-dichlorobenzyl)-3-(formylhydroxyamino)propanoyl]amide;

N-{2-[(Formylhydroxyamino)methyl]heptanoyl}-4-methyl-benzenesulfonamide;

N-{2-[(Formylhydroxyamino)methyl]heptanoyl}-4-phenoxy-benzenesulfonamide;

N-{2-[(Formylhydroxyamino)methyl]heptanoyl}-4-methoxy-benzenesulfonamide;

5-Methyl-pyridine-2-sulfonic acid {3-(3,4-dichlorophenyl)-2-[(formylhydroxyamino)methyl]propanoyl}amide;

N-{2-[(Formylhydroxyamino)methyl]hexanoyl}benzenesulfonamide;

5-Dimethylamino-naphthalene-1-sulfonic acid {2-[(formylhydroxyamino) methyl]hexanoyl}amide;

N-{2-[(Formylhydroxyamino)methyl]hexanoyl}-4-phenoxy-benzenesulfonamide;

5-Dimethylamino-naphthalene-1-sulfonic acid {2-[(formylhydroxyamino) methyl]-3-methyl-butanoyl}amide;

5-Dimethylamino-naphthalene-1-sulfonic acid {(R)-2-[(formylhydroxyamino)methyl]heptanoyl}amide;

5-Dimethylamino-naphthalene-1-sulfonic acid {2-[(formylhydroxyamino) methyl]pentanoyl}amide;

Biphenyl-4-sulfonic acid {2-[(formylhydroxyamino)methyl]pentanoyl}amide;

Biphenyl-4-sulfonic acid {2-[(formylhydroxyamino)-methyl]-4-methyl-pentanoyl}amide; and 5-Dimethylamino-naphthalene-1-sulfonic acid {2-[(formylhydroxyamino) methyl]-4-methyl-pentanoyl}amide; or a pharmaceutically acceptable salt thereof.

3. A method of treating a bacterial infection by administering to a subject in need of treatment a compound according to claim 1 or a pharmaceutically acceptable salt thereof.

4. A pharmaceutical composition comprising a compound according to claim 1 or a pharmaceutically acceptable salt thereof and a pharmaceutically acceptable carrier.

* * * * *